United States Patent
Soro (10) Patent No.: US 10,537,252 B2
(45) Date of Patent: Jan. 21, 2020

(54) RADIO FREQUENCY MAPPING USING MOBILE MONITORING DEVICES

(71) Applicant: General Electric Company, Schenectady, NY (US)

(72) Inventor: Stanislava Soro, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 130 days.

(21) Appl. No.: 15/605,743

(22) Filed: May 25, 2017

(65) Prior Publication Data
US 2018/0343596 A1    Nov. 29, 2018

(51) Int. Cl.
*A61B 5/021*    (2006.01)
*H04B 17/318*    (2015.01)
(Continued)

(52) U.S. Cl.
CPC ............ *A61B 5/021* (2013.01); *A61B 5/0006* (2013.01); *A61B 5/0024* (2013.01); *A61B 5/024* (2013.01); *A61B 5/0205* (2013.01); *A61B 5/0402* (2013.01); *A61B 5/0488* (2013.01); *A61B 5/14551* (2013.01); *H04B 17/318* (2015.01);
(Continued)

(58) Field of Classification Search
CPC combination set(s) only.
See application file for complete search history.

(56) References Cited

U.S. PATENT DOCUMENTS

| | | |
|---|---|---|
| 8,082,160 B2 | 12/2011 | Collins, Jr. et al. |
| 9,532,184 B2 | 12/2016 | Marti et al. |

(Continued)

OTHER PUBLICATIONS

Torabi, Narjes, et al.; "Cross-Layer Design for Prompt and Reliable Transmissions Over Body Area Networks"; IEEE Journal of Biomedical and Health Informatics, Jul. 2014, vol. 18, Issue: 4, pp. 1303-1316 (14 pages).

(Continued)

*Primary Examiner* — Zhitong Chen
(74) *Attorney, Agent, or Firm* — Andrus Intellectual Property Law, LLP (57) ABSTRACT

A system, includes a wireless communication network that transmits data over available radio frequency channels, one or more medical sensors that are associated with a patient and that detect physiological data from the patient, and one or more communication hubs associated with the patient and that receive the detected physiological data from the one or more medical sensors and scan the available radio frequency channels around the one or more communication hubs to generate radio frequency data indicative of a measured signal strength in each available radio frequency channel of the of available radio frequency channels. The one or more communication hubs wirelessly transmit the physiological data and the radio frequency data via one or more of the of available radio frequency channels. The system further includes a processor and a memory storing instructions, such that the instruction cause the processor to receive the radio frequency data and provide communications instructions to the one or more communication hubs to communicate the physiological data over a different available radio frequency channel based on the radio frequency data.

16 Claims, 7 Drawing Sheets

(51) Int. Cl.
*H04B 17/345* (2015.01)
*H04W 16/20* (2009.01)
*A61B 5/0402* (2006.01)
*A61B 5/0488* (2006.01)
*A61B 5/0205* (2006.01)
*A61B 5/1455* (2006.01)
*A61B 5/00* (2006.01)
*A61B 5/024* (2006.01)
*H04W 48/16* (2009.01)
*H04W 84/18* (2009.01)
*A61B 5/053* (2006.01)
*H04B 17/391* (2015.01)

(52) U.S. Cl.
CPC .......... *H04B 17/345* (2015.01); *H04W 16/20* (2013.01); *H04W 48/16* (2013.01); *A61B 5/053* (2013.01); *A61B 2505/03* (2013.01); *A61B 2505/07* (2013.01); *H04B 17/391* (2015.01); *H04W 84/18* (2013.01)

(56) References Cited

U.S. PATENT DOCUMENTS

| | | |
|---|---|---|
| 2013/0017791 A1 | 1/2013 | Wang et al. |
| 2013/0245387 A1 | 9/2013 | Patel |
| 2013/0337842 A1 | 12/2013 | Wang et al. |
| 2014/0287790 A1* | 9/2014 | Ichikawa .............. H04W 72/04 455/509 |
| 2015/0050888 A1 | 2/2015 | Baker et al. |
| 2015/0181282 A1* | 6/2015 | Majid ................ H04N 21/4384 725/38 |
| 2015/0238082 A1* | 8/2015 | Soro .................... A61B 5/0024 600/300 |
| 2016/0066788 A1 | 3/2016 | Tran et al. |
| 2016/0135206 A1* | 5/2016 | Wang ..................... H04W 4/70 370/329 |

OTHER PUBLICATIONS

Chevalier, Ludovic, et al.; "Optical Wireless Links as an Alternative to Radio-Frequency for Medical Body Area Networks"; IEEE Journal on Selected Areas in Communications, Sep. 2015, vol. 33, Issue 9, pp. 2002-2010 (9 pages).

* cited by examiner

RADIO FREQUENCY MAPPING USING MOBILE MONITORING DEVICES

BACKGROUND

The subject matter disclosed herein relates to systems and methods for assessing a radio frequency environment of medical devices.

Patient data, such as physiological parameters (e.g., heart rate, blood pressure, body temperature, etc.) indicative of the health of a hospital patient, is valuable information for a hospital and medical personnel responsible for the wellbeing of the hospital patients. The patient data (e.g., medical data) may be retrieved via certain monitoring devices that may include medical sensors. The monitoring systems may transmit the patient data over wireless links at or near real-time for further processing. In some instances, the wireless links may be more convenient than wired links, but may not provide the level of reliability of wired links, based at least in part on the fact that the quality of the wireless communication may deteriorate due to various causes, such as interferences, link obstruction, network congestion, etc. Furthermore, certain locations within the hospital may experience more problems (e.g., weak signals, signal loss, network congestions, etc.) than other locations due to uncontrolled interference, multipath signal propagation, signal absorption, uncovered areas, and the like, associated with a location.

Uncontrolled data loss via wireless links may result in delays in acquiring data for patient monitoring systems. As such, it may be beneficial to develop systems and methods that may improve the reliability of transmission of medical data.

BRIEF DESCRIPTION

In one embodiment, a system, includes a wireless communication network that transmits data over available radio frequency channels, one or more medical sensors that are associated with a patient and that detect physiological data from the patient, and one or more communication hubs associated with the patient and that receive the detected physiological data from the one or more medical sensors and scan the available radio frequency channels around the one or more communication hubs to generate radio frequency data indicative of a measured signal strength in each available radio frequency channel of the of available radio frequency channels. The one or more communication hubs wirelessly transmit the physiological data and the radio frequency data via one or more of the of available radio frequency channels. The system further includes a processor and a memory storing instructions, such that the instruction cause the processor to receive the radio frequency data and provide communications instructions to the one or more communication hubs to communicate the physiological data over a different available radio frequency channel based on the radio frequency data.

In another embodiment, a method includes receiving radio frequency data via a communication hub communicatively coupled to a medical sensor, such that the medical sensor is associated with a patient and detects physiological data from the patient. The communication hub receives the detected physiological data from the one or more medical sensors and scans available radio frequency channels in a wireless communication network around the communication hub to generate radio frequency data indicative of measured signal strength of a plurality of the available radio frequency channels in a wireless communication network, and the communication hub wirelessly transmits the radio frequency data via one or more available radio frequency channels of the available plurality of radio frequency channels. Furthermore, the method includes generating a radio frequency map based on the received radio frequency data, such that the radio frequency map includes the measured signal strength corresponding the each available radio frequency channel of the plurality of available radio frequency channels over time, the measured signal strength for each available radio frequency channel of the available radio frequency channels corresponding to each floor of a hospital environment, or any combination thereof. The method further includes providing communications instructions to the communication hubs to communicate the physiological data over a different available radio frequency channel based on the radio frequency map.

In yet another embodiment, a system includes a plurality of medical sensors and a plurality of communication hubs, where each medical sensor is associated with a respective patient and a respective communication hub of the plurality of communication hubs, such that each medical sensor detects physiological data from the patient and each communication hub receives the detected physiological data from the one or more medical sensors and scans a plurality of available radio frequency channels around each communication hub to generate radio frequency data indicative of measured signal strength of the plurality of available radio frequency channels in a wireless communication network and such that each communication hub is wirelessly transmits location data, the physiological data, and the radio frequency data via one or more of the plurality of available radio frequency channels. The system further includes a radio frequency monitor that includes a processor a memory storing instructions, such that the instructions cause the processor to receive the location data and the radio frequency data from the plurality of communication hubs, identify one or more congested radio frequency channels associated with an individual location, and provide communications instructions to one or more of the plurality of communication hubs associated with the individual location to communicate the physiological data to avoid the congested radio frequency channel.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements.

While the following discussion is generally provided in the context of mapping the radio frequency in hospital environments to facilitate the gathering and processing of information about the radio spectrum occupancy and the quality of communications across frequency channels in medical body area networks (MBAN), it should be appreciated that the present techniques are not limited to such medical contexts. Indeed, the provision of examples and explanations in such a medical context is only to facilitate explanation by providing instances of real-world implementations and applications. The present approaches may also be utilized in the mapping of the radio frequency of in industrial, scientific, and medical (ISM) radio bands, the wireless body area network (WBAN) of office environments, cellular radio bands, and so forth.

In particular, the present approach discusses radio frequency mapping using communication hub(s). The communication hubs that are associated with a particular patient and that serve as patient environmental monitoring devices (e.g., that may monitor radio frequency data including signal strength measures associated with a particular radio frequency channel) may be communicatively coupled to sensors to retrieve patient data indicative of physiological parameters and to act as a communications hub for the patient data. In some instances, the communication hubs may be located away (e.g., 5 meters) from the patient and sensors. In some instances, the patient data indicative of physiological parameters is analyzed and processed before being displayed (e.g., on a monitor, handheld device, etc.). This may include that the patient data be transmitted via a wired link to an external processor that includes the computing power and bandwidth to analyze the patient data arriving from the wired link. In some other instances, the patient data is transmitted wirelessly using the long range radio (such as Wi-Fi radio) via communication hubs to a hospital's communication infrastructure (e.g., Wi-Fi network, local area network (LAN), wide area network (WAN), etc.). The patient data may then be transmitted through the hospital's communication infrastructure to a radio frequency monitor for analysis and processing of the patient data. In certain embodiments, each individual patient is associated with a dedicated communication hub. When a patient moves within the hospital setting (e.g., to an imaging center, treatment center, etc.) the communication hub may travel with the patient.

In some instances, the communication between the communication hub(s) and the sensors may be done using short range wireless radio, operating, for example, in ISM spectrum (e.g., 433.05-434.8 MHz, 902-928 MHz, 2.4-2.5 GHz, and 5.725-5.875 GHz) radio band. Alternatively or in addition, the communication between the communication hub(s) and the sensors may be done using the MBAN spectrum, which occupies 2.36-2.4 GHz in the US and 2.835-2.5 GHz in the EU. Furthermore, the available radio band may be divided into a finite number of radio channels, and the hub and sensors use one channel at the time to communicate patient's data and other information.

The radio channels in the ISM band are commonly used by medical and non-medical devices (such as laptops, monitors, smart phones, tablets, etc.). The radio channels in the MBAN spectrum may be used by the patient monitoring medical devices, for example, when it is approved by the hospital. In both cases the medical and non-medical devices may access the available channels in uncoordinated ways. This may lead to situations where two or more devices try to transmit at the same radio channel at the same time, which can lead to packet collisions and data loss. This is the reason why it is important to find the best channel for patient's data and control exchange between the hub and the physiological sensors.

The present approach includes communication hubs that, in addition to sensing and/or receiving patient data, may also function to assess the radio frequency environment in the area surrounding the patient and any patient-associated sensors or devices. For example, a communication hub may scan radio frequency channels and collect information about the signal strength corresponding to each of the radio frequency channels. Furthermore, the communication hubs may collect data about the radio frequency environment over time and the location of the communication hub relative to the hospital. In some instances, when the radio frequency data (e.g., signal strength measures on a particular radio frequency channel) collected by the communication hubs is associated with an anomaly (such as an aberrant received signal strength associated with a particular radio frequency channel), the radio frequency monitor may also determine the sources (e.g., devices) contributing to the anomaly to correct the anomaly. As such, the reliability of the data transmitted via the radio frequency channels may be improved by correcting for the anomaly or sending information indicative of other radio frequency channels with low detected activity (such as the frequency channel with a low measured signal strength). An example of an anomaly may be a congested frequency channel with a high measured signal strength (e.g., due to high activity in the congested frequency channel). In some embodiment, the communication hub scans available radio frequency channels and measures the level of received power at a particular radio frequency channel at a given instance in time. If there are several transmissions from other wireless MBANs or other wireless devices going on in the vicinity of the communication hub, while the communication hub is scanning the channel, the measured signal strength may be higher. In some instances, it may efficient for the communication hub to operate in the cleanest channel (e.g., no detected transmissions/signals from other networks), such that the cleanest radio frequency channel may have a low received signal strength (e.g., a low intensity channel).

Figure 1:
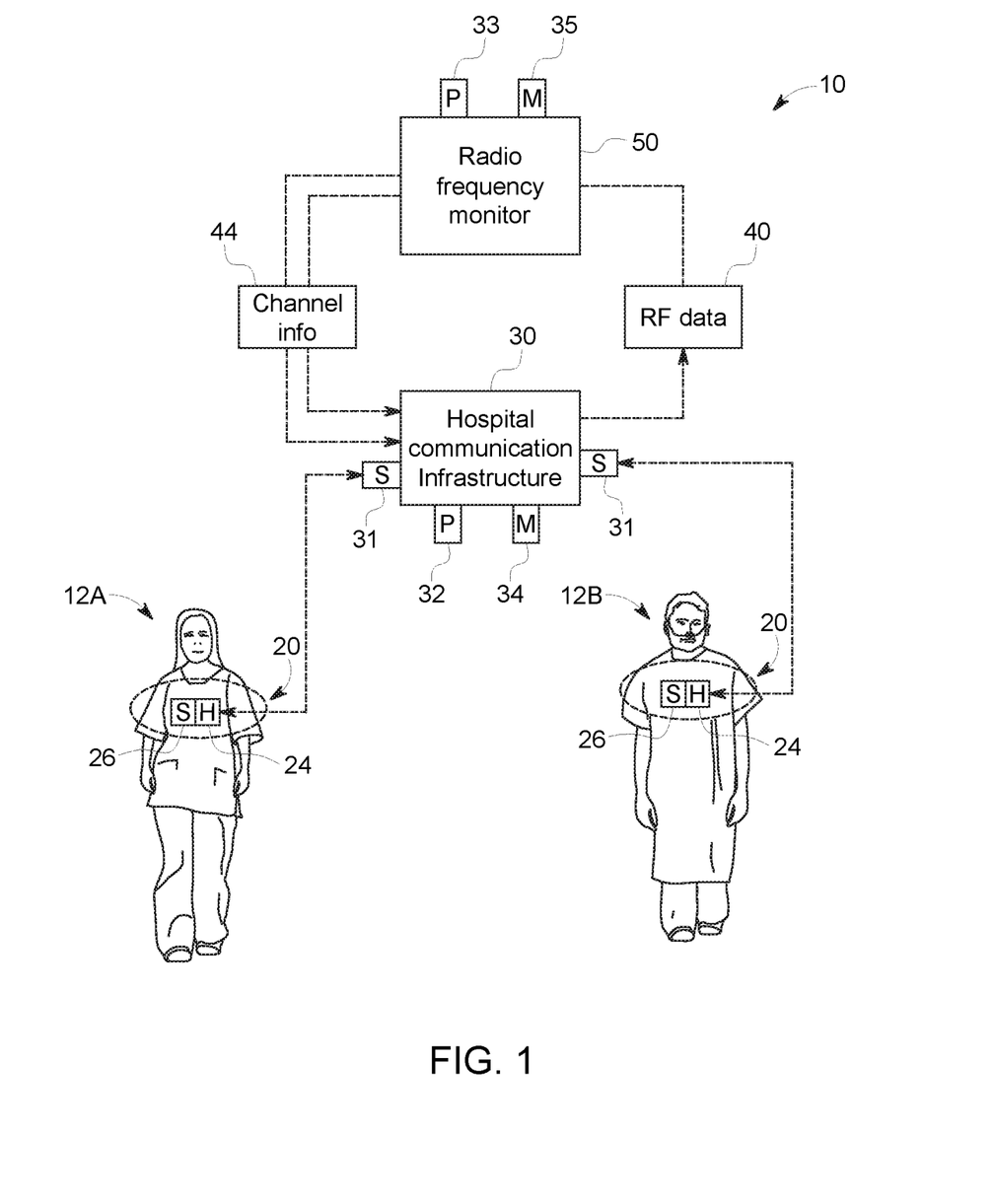
FIG. 1 is an embodiment of a schematic diagram of a wireless patient monitoring system, in accordance with an aspect of the disclosure.

By way of introduction, FIG. 1 illustrates a schematic diagram of an embodiment of a wireless patient monitoring system 10 of a hospital that utilizes one or more communication hubs 24 that operate in a MBAN 20. The MBAN 20 may facilitate short range wireless communication between the communication hub 24 and the sensors 26 using one operating radio frequency or radio channel. The hospital communication infrastructure 30 may in turn be communicatively coupled to the communication hubs 24 and a radio frequency monitor 50, among other devices such as laptops, desktops, mobile devices, and the like. As such, via communication with the hospital communication infrastructure 30, the communication hub 24 (e.g., and other devices communicatively coupled to the communication infrastructure) may send and receive data to and/or from the radio frequency monitor 50. For example, in some instances, the communication hub 24 may send patient data (e.g., indicative of physiological parameters) and/or radio frequency (RF) data 40 to the radio frequency monitor 50. Furthermore, the communication hub 24 may receive data (e.g., channel information 44) or communication instructions from the radio frequency monitor 50 related to the radio frequency environment.

More specifically, the illustrated embodiment includes two hospital patients 12. Each of the patients 12 includes a communication hub 24 and one or more medical sensors 26. It should be understood that the communication hub 24 and the medical sensor 26 may be separate devices communicatively coupled via the MBAN 20. In one embodiment, the medical sensor 26 is applied directly to the patient 12 while the communication hub 24 is attached or coupled to a patient bed or chair. In another embodiment, both the communication hub 24 and the medical sensor 26 are worn by the patient, and may be applied to the same or different body sites. In some instances, the medical sensors 26 may be radio-equipped devices that wirelessly send patient data (e.g., physiological data) to the communication hub 24. The medical sensor 26 may be any sensor that may monitor physiological parameters (e.g., blood pressure, heart rate, metabolic rate, blood oxygen concentration by volume of total blood, electrical activity produced by skeletal muscles of the patient, etc.) of the patient 12, such as a blood pressure sensor, an electrocardiogram (ECG) sensor, a pulse oximeter sensor, an electromyography (EMG) sensor, an inertial sensor, and the like. For example, the medical sensor 26 may be a wearable blood pressure sensor located on the wrist of a patient 12, such that the blood pressure sensor may provide data indicative of diastolic and systolic blood pressure. The patient data provided by the medical sensor 26 may be raw or calculated data. In some embodiments, the communication hub 24 may receive the patient data from the medical sensor 26 using a MBAN 20 (e.g., MBAN radio) (e.g., via a short range, low power radio).

In some embodiments, the communication hub 24 may receive patient data from the sensor 26 and transmit control signals to the sensors using low power frequency modulation (FM) signal. In some instances, as illustrated, the communication hub 24 also be worn by the patient 12. In other instances, the communication hub 24 may be located away from the medical sensors (e.g., and the patient 12). To continue the above mentioned example, a blood pressure sensor (e.g., medical sensor 26) may be worn on the wrist of a patient 12 and the communication hub 24 may be located adjacent the blood pressure sensor on the wrist on the patient 12. As such, the communication hub 24 may receive patient data from the sensor 26 when the communication hub is a distance (e.g., 1 meter, 2 meters, etc.) away from the medical sensor 26 using the low power short range radio, and then transmit the received patient data to the hospital communication infrastructure 30 using the long-range radio, such as Wi-Fi radio.

The hospital communication infrastructure 30 may refer to any infrastructure used to receive and transmit data among the various devices communicatively coupled to each other via the hospital communication system 30. In some embodiments, the hospital communication system 30 may be a Wi-Fi network, LAN, WAN, cellular, and the like. In some embodiments, the hospital communication system 30 may be a long range network, such that devices communicatively coupled to the hospital communication system 30 may be far away from the access point and remain connected to it. Furthermore, the hospital communication infrastructure may have enough bandwidths to accommodate (e.g., communicatively couple with) a wide variety of devices. For example, the communication hub 24 may be coupled to various computing devices (e.g., laptops, desktop computers, mobile devices, tablets, etc.) at the hospital via the hospital communication infrastructure 30 so that medical personnel may have patient data received from the communication hub 24 readily available. Furthermore, the hospital communication system 30 may include many Wi-Fi access points that facilitate the transmission of data between the hospital communication infrastructure 30 and the devices communicatively coupled to the hospital communication infrastructure 30 (e.g., Wi-Fi network). The hospital communication infrastructure 30 may include sensors 31 (e.g., receivers, Wi-Fi access points, etc.) that may receive/send data from any devices communicatively coupled to the hospital communication infrastructure 30.

As illustrated the radio frequency monitor 50 may gather and process information about the radio spectrum occupancy and quality of the communication across frequency channels in MBAN frequency bands and locations within the hospital over time. That is, based on the radio frequency data 40 received from the communication hub 24, the radio frequency monitor 50 may be able to generate the radio frequency maps of FIG. 4. As mentioned in detail below, the communication hub 24 may receive radio frequency channel information 44 that may be included in the radio frequency maps to determine which radio frequency channels to use. That is, based on the radio frequency data (e.g., signal strength measures on a particular radio frequency channel and on the particular location) provided by the communication hubs 24, the radio frequency monitor 50 may understand the radio frequency environment in which communication hub 24 operates and provide the radio frequency channel(s) that are not congested to the MBAN 20. As such, the RF map (from radio frequency monitor 50) may provide information about the radio frequencies used for transmission of physiological data between patient-worn sensors and the hub.

Figure 2:
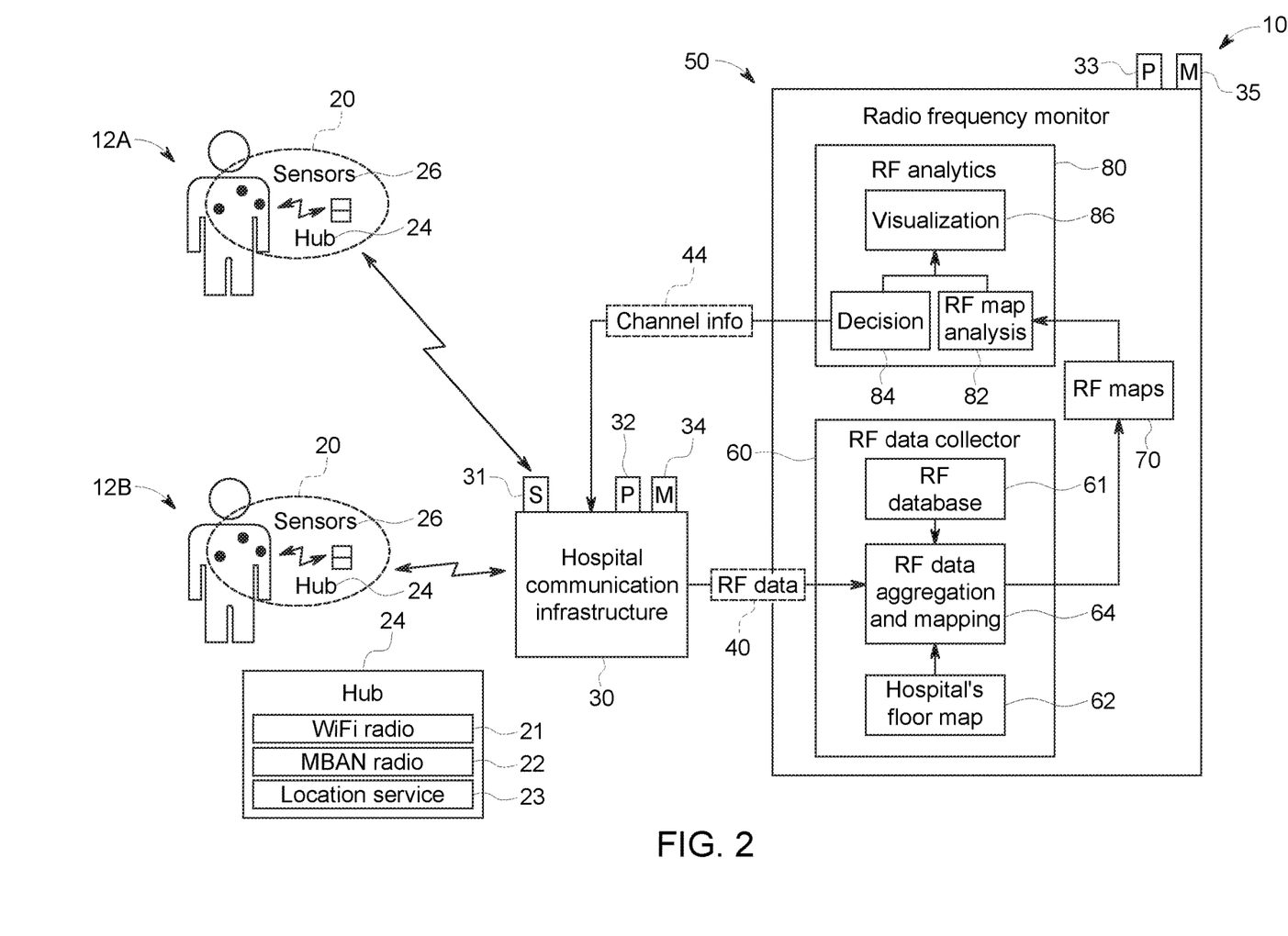
FIG. 2 is an embodiment of a schematic diagram of the wireless patient monitoring system of FIG. 1, in accordance with an aspect of the disclosure.

Turning to FIG. 2, illustrated is a detailed schematic diagram of the wireless patient monitoring system of FIG. 1. As mentioned above, patients 12A and 12B, (collectively called "patients 12") may each include at least one medical sensor 26 and communication hub 24 that are communicatively coupled via short range MBAN radio 22. The communication hub 24 may be communicatively coupled to the radio frequency monitor 50 (e.g., among other device) via the hospital communication infrastructure 30. As mentioned above, the radio frequency monitor 50 may receive radio frequency data 40 from the communication hub 24 and send channel information 44 to the communication hub 24.

In more detail, the communication hub 24 may include a Wi-Fi radio 21, such that the Wi-Fi radio 21 may transmit patient and radio frequency data 40 through the hospital communication infrastructure 30 to facilitate the wireless communication and exchange of data with the hospital communication infrastructure 30. As illustrated, the communication hub 24 includes an MBAN radio 22, such that the MBAN radio 22 may transmit and receive data and control messages from the sensors 26. That is, the MBAN radio 22 may facilitate the wireless communication and exchange of data with the sensor(s) 26. Furthermore, the communication hub 24 may include a location service 23 that may determine or provide information about the location communication hub 24. That is, the communication hub 24 may be capable of determining its location. For example, the communication hub 24 may include a real time location service (RTLS), global positioning system (GPS), assisted GPS, inertial sensors, terrestrial transmitters, and the like. In other embodiment, the communication hub 24 may facilitate communication with location beacons and may provide the beacon information to the radio frequency monitor 50.

Furthermore, in some embodiments, the communication hub 24 is used facilitate continuous monitoring of a patient 12 by receiving data indicative of physiological parameters from sensors 26. In some instances, the data indicative of physiological parameters may be communicated to the communication hub 24 via the MBAN radio 22. The communication hub 24 may send this data to the radio frequency monitor 50 (e.g., in the hospital) via the Wi-Fi radio 21, which may allow for the exchange of data between the communication hub 24 and the hospital communication infrastructure 30. In some embodiments, the communication hub 24 scans radio frequency channels when the communication hub is not communicating with sensor(s) 26. In some embodiments, the scanning performed by the communication hub 24 may be a low power operation, during which the communication hub 24 (e.g., or MBAN radio 22) measures the received signal strength (RSS) at the particular center frequency corresponding to the scanned radio frequency channel. Information indicative of the scanned radio frequency channels may be forwarded to the radio frequency monitor 50.

The radio frequency monitor 50 may build radio frequency maps 70, based on the information indicative of the scanned radio frequency channels. Channel information 44 (e.g., the information about the particular radio frequency channel associated with the communication hub 24) may be sent to the communication hub 24. In some embodiments, the resolution of the radio frequency maps 70 may depend on the precision of the location service 23 used by the communication hubs 24. For example, in the case of Real Time Locating Systems (RTLS) based on RF sensors (e.g., such as Bluetooth, the location precision error may be approximately 3 meters). In the case of ultra-wideband RTLS system the precision error may be approximately 1 feet. In case of the camera-based location system the location precision error may be less than one feet.

The channel information 44 may include information representative of the signal strength of the radio frequency channels at the particular location, obtained by reported measurements from multiple hubs. In some instances the channel information 44 may be retrieved at any time intervals (e.g., 5 milliseconds (ms), 10 ms, 100 ms, 1 second (s), etc.) by the communication hub 24. In some embodiments, the periodic time intervals may be long enough to provide enough time to sample the radio frequency signal and provide the received signal strength value. In some instances, when the communication hub 24 is not transmitting data to the hospital communication infrastructure 30, the communication hub 24 may receive channel information 44 (e.g., the information from the radio frequency maps 70 about the particular radio frequency channel associated with the communication hub 24).

In some embodiments, communication hub 24 may operate on one out of multiple channels (e.g. 40 channels in ISM band (2400-2480 MHz)). As such, to assess the signal level on other available channels the communication hub 24 may decide which radio frequency channel(s) to scan. The communication hub 24 may scan those radio frequency channels in some pseudo-random order. Alternatively, the communication hub 24 may use some channel ranking method to decide which radio frequency channel to scan.

For example, the communication hub 24 may have information that its corresponding Wi-Fi radio 21 is connected to the Wi-Fi access point which operates using particular Wi-Fi channel. In some instances, since the Wi-Fi access point may handle high channel traffic and the Wi-Fi channel occupies 20 MHz of the available ISM bandwidth, the hub 24 may decide not to scan MBAN radio frequency channels that overlap with this Wi-Fi channel.

In other example, the hub 24 may decide to scan the available MBAN radio frequency channels based on the time when each channel was scanned. In this case the communication hub 24 may first scan the channel, which it scanned for the least amount of time.

In another example, the communication hub 24 may internally store (e.g., in its memory) the received signal strength (RSS) for each channel it previously scanned. Then the communication hub 24 may decide to rescan the channels which have higher signal strength at a quicker rate, which indicates the presence of other active devices on these channels.

In another example, the communication hub 24 may not receive some of the patient's data via the one or more sensors 26, while the one or more sensors 26 are transmitting data using a particular frequency channel. The communication hub 24 may then decide to scan this particular channel for some time period to collect information indicative of whether this channel in being used often by other wireless devices.

Moreover, as illustrated, the radio frequency monitor 50 includes a radio frequency data collector 60 that collects the radio frequency inputs (e.g., radio frequency data 40) from the communication hub 24 corresponding to the patients 12. That is, the radio frequency data collector 60 may receive the radio frequency data and associate it with the hospital's floor map (block 62). For example, the radio frequency data collector 60 of radio frequency monitor 50 may receive the physiological data via the hospital communication infrastructure 30 along the Wi-Fi radio 21 with associated location on the hospital's floor map (e.g., via the location service 23). The radio frequency data collector map 60 may assign a received signal strength (RSS) indication to the radio frequency channel and associated location on the hospital's floor map during the time intervals data is collected, as discussed in more detail below. Furthermore, the radio frequency data collector 60 may receive data from a radio frequency data base 61. In some embodiments, the radio frequency database 61 may include information indicative of all the devices which the radio frequency monitor 50 has information about. In some embodiments, the radio frequency data base 61 may include information indicative of devices registered with the radio frequency database 61. For example, the radio frequency database 61 may include information about the communication hubs 24, Wi-Fi access points, or any other suitable medical/non-medical devices.

Furthermore, the radio frequency data collector 60 may compile the aggregate from multiple communication hubs 24, which are registered in the radio frequency database 61 and begin mapping the radio frequency data (block 64). In some embodiments, the radio frequency data collector 60 may take information indicative of the hospital's floor map and assign radio frequency data (e.g., RSS indications) to the corresponding locations of the hospital's floor. For example, the radio frequency data collector 60 may receive radio frequency data 40, such as the location (e.g., coordinates and hospital floor), time, RSS indication, and frequency associated with each measurement taken by the communication hub 24. The radio frequency data collector 60 may process the data (e.g., via processor 33) to generate radio frequency maps 70.

Overtime, the radio frequency monitor 50 may use the radio frequency data 40 to build radio frequency maps 70. In some embodiments, the radio frequency monitor 50 may build radio frequency maps 70 corresponding to each floor of the hospital floorplan. In certain instances, the operating frequency can be presented with one radio frequency map 70. Furthermore, the processor 33 of the radio frequency monitor 50 may continuously update the radio frequency map(s) 70 with new information representative of the quality of the radio channels received from the communication hubs 24 corresponding to the patients 12. In some embodiments, the radio frequency maps 70 may be updated at or near real time to, for example, reflect changes in the radio frequency data 40 received by the radio frequency monitor 50.

Furthermore, while the radio frequency maps 70 are being updated, in some embodiments, the radio frequency maps 70 and its associated data may be analyzed by radio frequency analytics 80 of the radio frequency monitor 50. As illustrated, the radio frequency analytics 80 provides an analysis of the radio frequency map (block 82) to, for example, understand the radio frequency environment in which medical equipment (e.g., communication hub 24, laptops, hand-held devices, etc.) operates. As a further example, the analysis of the radio frequency map (block 82) may include discovering and analyzing problems with certain operating channels, identifying problems (e.g., such as a presence of strong signals that indicate the presence of other, interfering devices), determining a quality of the radio frequency coverage corresponding the radio frequency channels, and the like for networks at certain times of the day. In this manner, the map may represent radio frequency environment information on a per-room or per-location basis. Accordingly, any identified anomalies may be tracked to a particular location. For example, in a shared room scenario, the radio frequency monitor 50 may identify communication disruption as a result of congestion at a particular radio frequency channel based on radio frequency data (e.g., signal strength measures on a particular radio frequency channel) from one or more communication hubs 24. Communication frequencies for patient data from all medical sensors 26 associated with the shared room may be assigned to avoid frequency and/or time conflict. That is, each communication hub 24 in the room may receive instructions to transmit patient data at a particular time (e.g., transmit in an assigned time range) and/or a particular frequency (e.g., transmit at an assigned frequency) to avoid communications conflict (i.e., to avoid same time and/or same frequency communication between different communication hubs 24 or to avoid congested frequencies)

That is, after the radio frequency analytics 80 analyzes the radio frequency maps 70, the radio frequency analytics may provide an output, such as a decision 84, based at least in part on the radio frequency map analysis (block 82). The decision 84 may be based on determining the problem and/or a solution to the problem at a location, or determining the least busy radio frequency channel (e.g., the radio frequency channel corresponding to the lowest RSS). In some embodiments, the decision 84 may provide a structured frequency assignment and zoning for the hospital devices engaging with the hospital communication infrastructure 30. For example, the decision 84 may include providing the communication hub 24 with a radio frequency channel with best radio frequency channel (e.g., the radio frequency channel with the lowest RSS of the detected signal) and which is not used in time to, for example, enhance the reliability by which the physiological data is transferred wirelessly throughout the wireless patient monitoring system 10.

Furthermore, in some embodiments, the radio frequency monitor 50 may send a request to communication hub 24 to scan a certain frequency channels. In some instances, the radio frequency monitor 50 may send channel information 44 that includes the frequency channels with a low detected activity, i.e., with low measured signal strength and that share the location of (e.g., are in close proximity to) the communication hub 24. That is, when a patient 12 moves throughout a hospital, such that the communication hub 24 also moves with the patient 12, the radio frequency monitor 50 may send channel information 44 that includes the frequency channels with a low measured signal strength and that share the new location of (e.g., are in close proximity to) the communication hub 24. In some instances, when a patient moves throughout the hospital, the channel scanning information collected by the communication hub 24 (e.g., the channel scanning performed by the communication hub 24) is time stamped and paired with the location information of the communication hub. In turn, the time stamp and corresponding location (e.g., and other suitable information corresponding to the communication hub 24) is sent to the radio frequency data collector 60.

Furthermore, the radio frequency analytics 80 may provide a visualization 86 of the radio frequency map and/or the decision. For example, the radio frequency analytics 80 may provide a visualization 86 of radio frequency maps 70 corresponding to locations (e.g., each floor of the hospital), as described in detail below with regards to the discussion of FIG. 3. Furthermore, visualization 86 may include an RSS map corresponding to the various frequency channels of the wireless patient monitoring system 10, as illustrated in FIG. 4. In further embodiments, it should be noted that the visualization 86 may be communicated to a device with a display via the hospital communication device 30 and displayed on the device. Furthermore, the visualization 86 may include any visual representation associated with the radio frequency maps 70 and the various components of the patient monitoring system 10.

Figure 3:
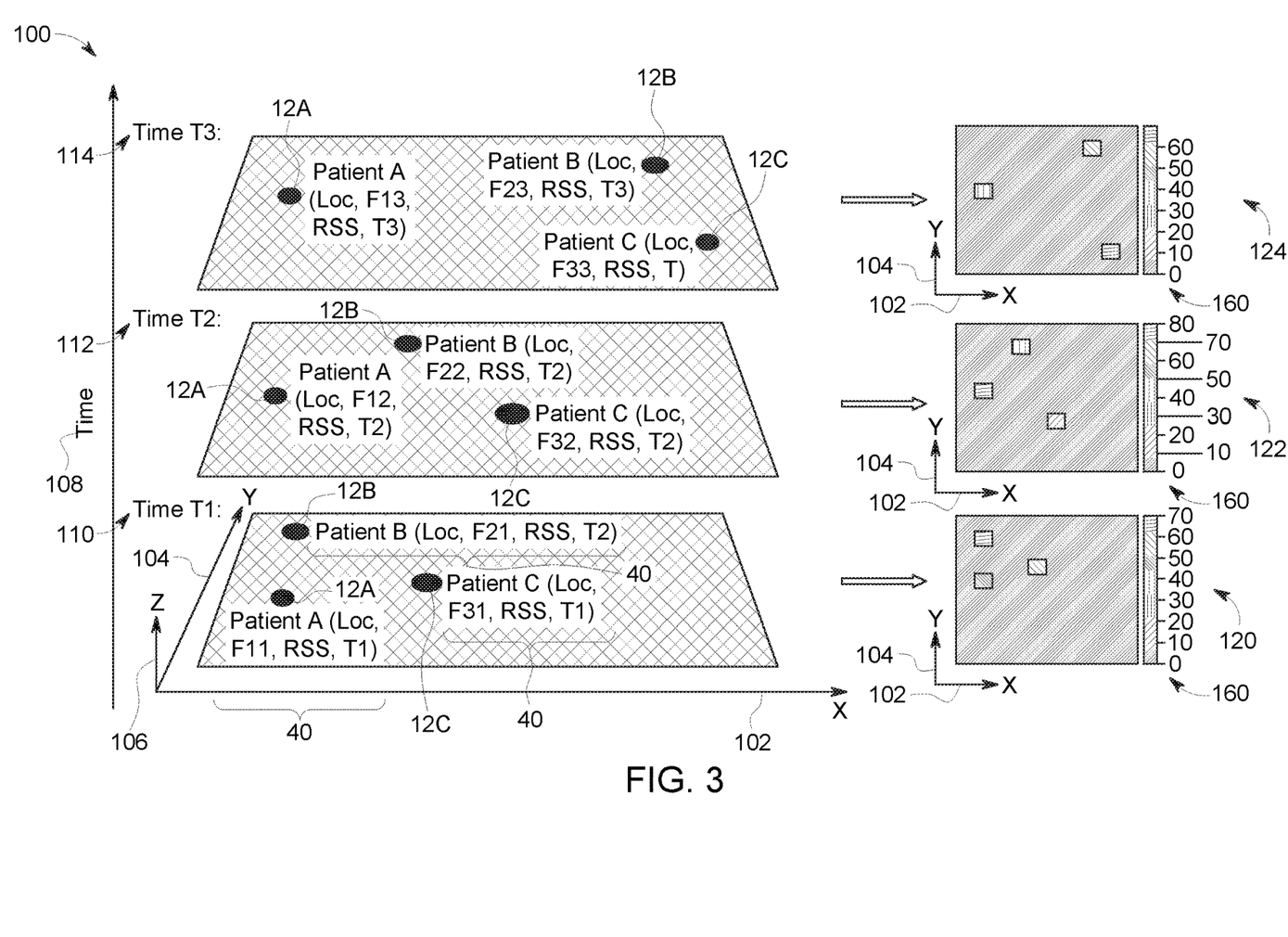
FIG. 3 is an embodiment of a visualization schematic of radio frequency maps, in accordance with an aspect of the disclosure.
Figure 4:
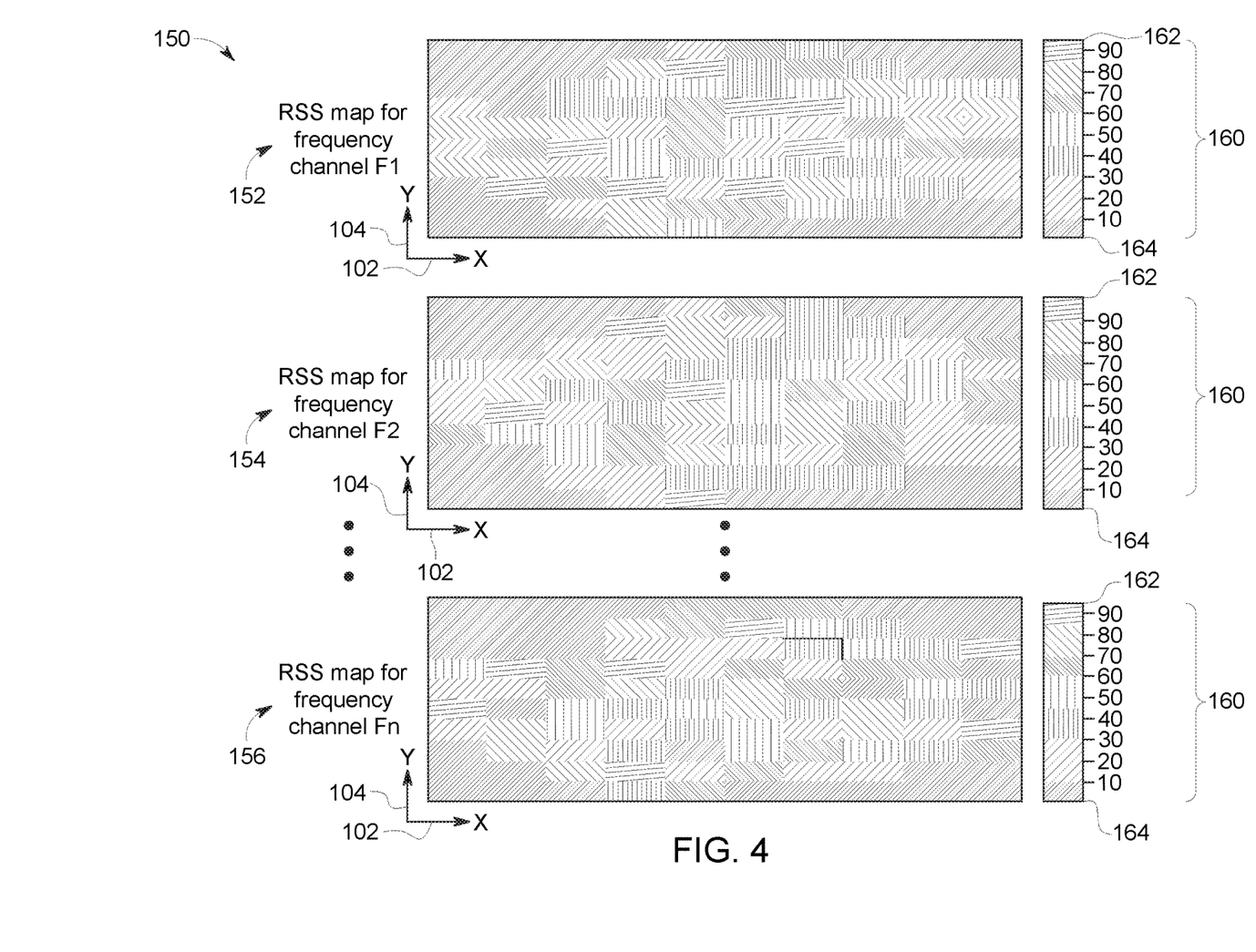
FIG. 4 is an embodiment of a visualization schematic of radio frequency maps corresponding to the radio frequency channels of the wireless patient monitoring system of FIG. 1, in accordance with an aspect of the disclosure.

Turning to FIG. 3, illustrated is a schematic of a visual representation 100 of radio frequency (RF) maps for a floor of the hospital over time. In some embodiments, the visual representation 100 of radio frequency (RF) maps for a floor of the hospital over time 108 may be generated as a visualization 86 based on the radio frequency data 40 analyzed by the radio frequency analytics 80. As illustrated, the radio frequency map visual representation 100 may include plots of radio frequency data 40 corresponding to three patients (12A, 12B, and 12C) on a floor (e.g., hospital floor) respectively at a time T1, a time T2, and a time T3. For example, as illustrated, the radio frequency map visual representation 100 may include radio frequency data 40 associated with each patient at a time T1 on a first plot 110, a time T2 on a second plot 112, and a time T3 on a third plot 114. In some embodiments, the plots of radio frequency data may include an x-coordinate 102, a y-coordinate 104, (e.g., collectively comprising the floor dimensions of the hospital), and a z-coordinate 106 (e.g., corresponding to the height away from the floor of the hospital).

The radio frequency data 40 may include a coordinate location (Loc) (e.g., x-coordinate 102, y-coordinate 104, z-coordinate 106) corresponding to the patients (12A, 12B, and 12C), a radio frequency channel information (e.g., F11, F12, F13, etc.) corresponding to patients, RSS indications corresponding to the patients, and a time associated with the above mentioned radio frequency data 40. For example, in the first plot 110, patient 12A reports radio frequency data 40, including a respective location (Loc), radio frequency channel information (e.g., F11), RSS indication (RSS), at a first time (T1). Furthermore, a first radio frequency map 120 corresponding to the patients 12 at a time T1 may include the location of the patients (e.g., represented by x-coordinates 102 and the y-coordinates associated with the squares of the first radio frequency map 120) and RSS values corresponding to the communication hubs 24 of the patients 12 (e.g., represented by the color of the squares based on the gradient scale 160).

At time T2, a second plot 112 may include a new set of radio frequency data 40 at time T2. As illustrated, the position (Loc) of the three patients is changed for time T2 relative to time T1 (e.g., because the patients 12 may have moved since a measurement was taken at T1). As such, the radio frequency data 40 corresponding to each of the three illustrated patients 12 may be updated to reflect new values radio frequency data 40 for time T2. For example, as illustrated in the second plot 112 the radio frequency data for patient 12A may be updated to reflect a second location (e.g., Loc), second radio frequency channel information (e.g., F12), and a second RSS indication (RSS) at a time T2. In the illustrated embodiment, the radio frequency map 122 corresponding the radio frequency data 40 for the three patients 12 at time T2, may include a second location of the patients (e.g., represented by x-coordinates 102 and the y-coordinates associated with the squares of the first radio frequency map 120) and second RSS values corresponding to the communication hubs 24 of the patients 12 (e.g., represented by the color of the squares based on the gradient scale 160).

Furthermore, as illustrated, the third plot 114 may include a third set of radio frequency data 40 corresponding to a time T3. The radio frequency data 40 may include location, radio frequency channel information, and a RSS indication for each of the three patients 12 at time T3. As such, the radio frequency map 124 corresponding to time T3 may be generated. In some embodiments, floor plots (e.g., similar to 110, 112, and 114) and corresponding radio frequency maps (e.g., 120, 122, and 124) at certain time intervals (e.g., T1, T2, T3, etc.) may be generated by including radio frequency data 40 that is received by the radio frequency monitor 50.

In some embodiments, the information indicative of radio frequency (RF) maps for a floor of the hospital over time 108 may be analyzed by the radio frequency analytics 80 to generate information about the wireless patient monitoring system 10. For example, the radio frequency maps may be used to identify available radio frequency channels, such that the available radio frequency channels may allow for the transmission of data between the sensors 26 and the communication hub 24. In some instances, after identifying the available radio frequency channels, the information indicative of the available radio frequency channel may be sent to the communication hub 24 as channel information 44. As such, in some instances, the communication hub 24 may switch transmitting data via a certain radio frequency channel to the newly identified radio frequency channel, if, for example, the radio frequency channel experiences an anomaly (e.g., becomes congested, experiences an excessive packet loss, etc.).

In some embodiments, the radio frequency maps may also be analyzed by the radio frequency analytics 80 to determine a next set of radio frequency channels the communication hub 24 should scan. That is, the radio frequency monitor 50 may send as channel information 44 a new set of radio frequency channels for the communication hub 24 to scan based on the location of the communication hub 24 and the activity of the radio frequency channels (measured in high or time variable RSS on these channels). As such, in some embodiments, the radio frequency monitor may obtain information associated with particular radio frequency channels to update the radio frequency maps.

In some instances, the radio frequency analytics 80 may provide more comprehensive at or near real-time situational awareness information to the radio frequency monitor 50\ The situational awareness information provide more detail level information on the causes of the particular problem that is detected by the radio frequency analytics 80, such as information obtained by analysis of the radio frequency data collected over a short period of time or a long period of time by many communication hubs 80 at the certain location. For example, the situational awareness information may include data on the overall radio frequency environment in areas on the hospital where patients 12 spend most of their time. The radio frequency analytics 80 may determine the radio spectrum and indications as to whether there are problems at certain locations in the hospital and/or over time. For example, if physiological data from the patient 12 is not being received by the communication hub, the situational awareness information may show whether several other communication hubs 24 operate at the same channel at the same time in the vicinity of each other, which may indicate network congestion problem (e.g., an anomaly).

As such, in some embodiments, the radio frequency monitor 50 may determine if the data loss is caused by channel congestion (e.g., multiple other devices being active at the same radio frequency channel in nearly the same time). The situational awareness information may also include radio frequency data 40 indicative of a usage pattern of the radio frequency channels. For example, the radio frequency analytics 80 may determine whether the Wi-Fi access points affect the channels close to it, based on situational awareness information, such as how commonly affect the radio frequency channels close to it. In more detail, the location of the Wi-Fi access point is fixed and may be known on the radio frequency map 70. The access point may use the Wi-Fi channels, and may overlap with some of the radio frequency channels used by communication hubs 24. Therefore, if the communication hub 24 is close to the Wi-Fi access point, and if the communication hub 24 scans the radio frequency channels that overlap with radio frequency channel at which access point operates, it may provide information on how much of the Wi-Fi access point occupies the MBAN radio frequency channels, both in terms of signal strength and channel occupancy time with respect to current position of the communication hub 24.

Turning to FIG. 4, illustrated is a visual representation 150 of an embodiment of the RSS map corresponding to the frequency channels of the wireless patient monitoring system 10. The visual representation includes a first RSS map 152 corresponding to frequency channel F1, a second RSS map 154 corresponding to frequency channel F2, and an nth RSS map 156 corresponding to frequency channel Fn, where n is the total number of frequency channels. Furthermore, the illustrated RSS maps (152, 154, and 156) show RSS indications for the hospital floor area. That is, the radio frequency data 40 may be stamped in time and based on the location of the communication hub 24, which may be used to generate the illustrated RSS maps as a two dimensional map, which is updated at or near real time with newly received radio frequency data 40.

The illustrated embodiment includes radio frequency data 40 corresponding to the illustrated frequency channels that is new (e.g., recently updated and corresponding to a time in or near the present). That is, the color gradient scale 160 corresponding to each of the illustrated RSS maps (152, 154, and 156) provide a scale for the RSS corresponding to areas on the hospital floor space depicted on the RSS maps. In more detail, the illustrated embodiment includes a light color 162 that corresponds to a high RSS and a dark color 164 that corresponds to a low RSS. In some embodiments, as the color gradient progresses from the light color 162 to the dark color 164, the RSS becomes lower. In further embodiments, any scale or legend indicative of RSS strength, instead of the color gradient scale 160, may be used for the RSS maps.

In some instances, the radio frequency monitor 50 may also produce other maps indicative of the radio frequency data 40 and the radio frequency channels. For example, the radio frequency monitor 50 may generate a plot of average signal values over a time interval for each (e.g., or any number) of the radio frequency channels, a table of minimum and maximum signal values over a time interval, and the like. In addition, the radio frequency monitor 50 may store (e.g., in memory 35) radio frequency data 40 and develop trends regarding radio frequency signal and its relationship to location and time.

Figure 5:
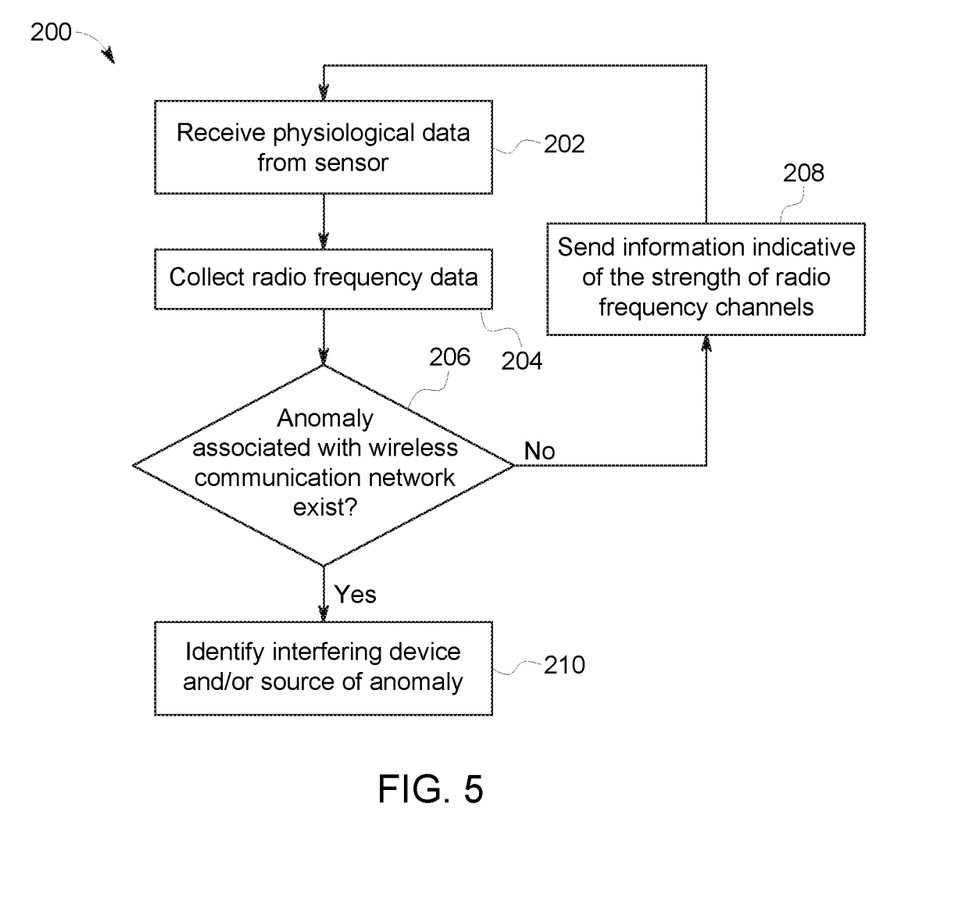
FIG. 5 is a flow diagram depicting an embodiment of a process of radio frequency assessment that may be used in conjunction with the system of FIG. 1, in accordance with an aspect of the disclosure.

FIG. 5 is a flow diagram 200 depicting an embodiment of a process whereby the radio frequency monitor 50 of the wireless patient monitoring system 10 may send channel information 44 to the communication hub 24 via the hospital communication infrastructure 30. In some instances, as discussed above, the radio frequency monitor 50 may collect radio frequency data 40 from the environment, and identify an anomaly associated with the radio frequency environment based on the received radio frequency data 40. When an anomaly (e.g., such as a high measured signal strength of a radio frequency channel due to an overload of activity in the radio frequency channel, long radio frequency channel occupancy time, etc.) is detected by the radio frequency monitor, in some embodiments, the radio frequency monitor 50 may identify the source of the anomaly (e.g., the interfering device). The radio frequency monitor 50 may then send information indicative of the radio frequency channels to the communication hub 24.

In more detail, as illustrated in FIG. 5, the radio frequency monitor 50 may receive physiological data from the medical sensors 26 (process block 202). That is, in some embodiments the communication hub 24 and the radio frequency monitor 50 may both be communicatively coupled to the hospital communication infrastructure 30. As such, the communication hub 24 and the radio frequency monitor 50 may transmit data between each other. For example, after the medical sensor 26 generates patient data and communicates the patient data to the communication hub 24, the communication hub 24 may transmit the patient data to the hospital communication infrastructure 30. In certain embodiments, the patient data may include physiological parameters or data indicative of the physiological parameters (e.g., blood pressure, heart rate, metabolic rate, blood oxygen concentration by volume of total blood, electrical activity produced by skeletal muscles of the patient, etc.) of the patient 12. In some instances, the radio frequency monitor 50 may receive the patient data via the hospital communication infrastructure 30. The radio frequency monitor 50 may alternative or additionally collect radio frequency data 40.

That is, the radio frequency monitor 50 (process block 204) may collect radio frequency data 40 from the radio frequency environment of the wireless patient monitor system 10. In some embodiments, the radio frequency monitor 50 may use information indicative of the hospital's floor map and assign radio frequency data 40 the corresponding locations of the hospital's floor. For example, the radio frequency monitor 50 may receive radio frequency data 40, which may include the location (e.g., coordinates and hospital floor), time, RSS indication, and associated frequency channel. The radio frequency monitor 50 may process the data (e.g., via processor 33) to generate the radio frequency maps of FIGS. 3 and 4. In alternative embodiments, the radio frequency monitor may collect radio frequency data 40 and physiological parameters via the hospital communication infrastructure 30.

After collecting the radio frequency data 40 from the communication hub 30, the radio frequency monitor 50 may determine whether an anomaly associated with the radio frequency environment exists (decision block 206). In some embodiments, an anomaly associated with the radio frequency environment may be a high measured signal strength for a radio frequency channel (e.g., a congested radio frequency channel). For example, the radio frequency monitor 50 may determine whether the measured signal strength corresponding to the radio frequency channels of the radio frequency environment is above a threshold value. When the measured signal strength is above the threshold value, the radio frequency monitor 50 may determine that an anomaly exists, and when the measured signal strength is below the threshold value, the radio frequency monitor 50 may determine that an anomaly does not exist. Furthermore, the anomaly may be a drop in data being transmitted via the hospital communication infrastructure 30 across a certain radio frequency channel. In further embodiments, the anomaly may be any event or component of the wireless patient monitoring system 10 that may contribute to a potential loss of data transmission.

When the radio frequency monitor 50 identifies an anomaly associated with the radio frequency environment, the radio frequency monitor 50 identify the source of the anomaly (process block 210). In some embodiments, identifying the source of the anomaly may include identifying the device that may be contributing to the anomaly. For example, the radio frequency monitor 50 may determine that a radio frequency channel has a measured signal strength above a certain threshold value, such that the radio frequency monitor flags the radio frequency channel and its high measured signal strength as an anomaly. The radio frequency monitor 50 may use the radio frequency maps and/or any of the radio frequency data 40 to identify the source (e.g., device) contributing to the anomaly.

In some instances, identifying the interfering device by the radio frequency monitor 50 may include identifying a potential solution to, for example, potentially prevent the loss of data transmission. In some embodiments, the radio frequency monitor may send information regarding free (e.g., available radio frequency channels) with a low (e.g., below a threshold value) measured signal strength. As such, when the radio frequency monitor 50 sends this information to the communication hub 24, the communication hub 24 may transmit data through a different radio frequency channel. In some embodiments, when the communication hub 24 transmits data through a different radio frequency channel may be a potential solution to potentially prevent the loss of data transmission and may cause the communication hub 24 to avoid congested channels.

After the radio frequency monitor 50 identifies interfering devices and/or sources of the anomaly to, for example, potentially prevent the loss of data transmission, the radio frequency monitor 50 may send information indicative of the strength of the radio frequency channels to the communication hub 24 (process block 208). As mentioned above, the information indicative of the measured signal strength of the radio frequency channels of the radio frequency environment may include a set of available radio frequency channels with a lower signal strength than the current radio frequency channel the communication hub 24 may be using to transmit data. Generally, the radio frequency monitor 50 may send any channel information 44, as described in detail above, to the communication hub 24 or any other suitable device.

Furthermore, it should be noted that the radio frequency monitor 50 may send information indicative of the strength of the radio frequency channels (e.g., to the communication hub 24) (process block 208) when an anomaly associated with the radio frequency environment is not identified (e.g., does not exist). In some embodiments, this may include the radio frequency monitor 50 continuing to send the communication hub 24 the channel information 44 associated with the current radio frequency channel the communication hub may be using to transmit data.

Figure 6:
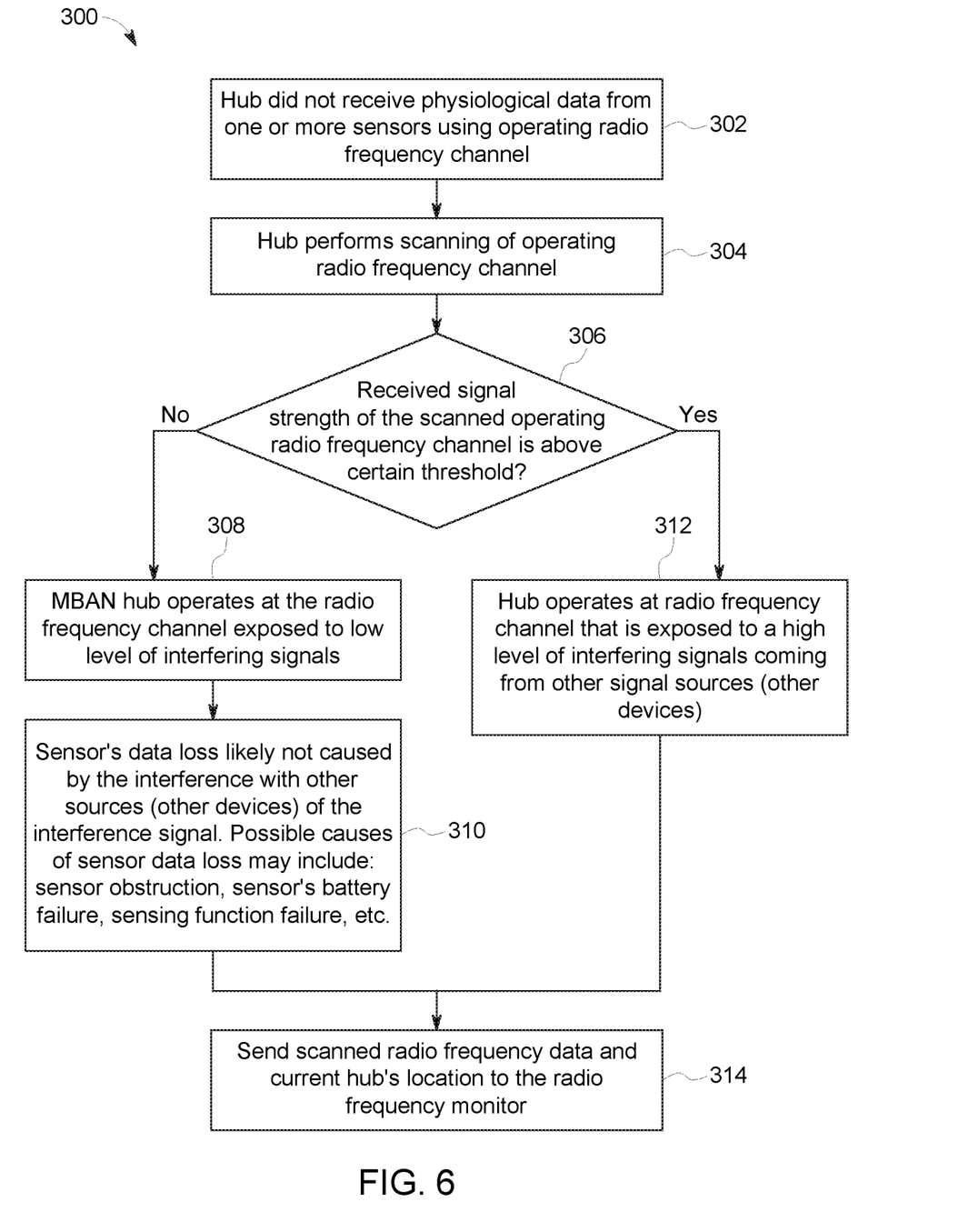
FIG. 6 is a flow diagram depicting an embodiment of a process performed by a communication hub that may be used in conjunction with the system of FIG. 1, in accordance with an aspect of the disclosure.

Turning to FIG. 6, depicted is a flow diagram 300 of an embodiment of a process performed by a communication hub 24 that may be used in conjunction with the system of FIG. 1. In more detail, when the communication hub 24 does not receive (e.g., exchange) physiological data from the one or more sensors 26 using the operating radio frequency channel (process block 302), the communication hub 24 scans the operating radio frequency channel (process block 304). After scanning the operating radio frequency channel, the communication hub 24 measures the received signal strength of operating radio frequency. In some embodiments, the communication hub 24 determines whether the received signal strength (RSS) of the scanned operating radio frequency channel is above a certain threshold (decision block 306).

When the RSS of the scanned operating radio frequency channel is not above (i.e., below) a certain threshold, the communication hub 24 may determine that it is operating at a radio frequency channel exposed to a low level of interfering signals (process block 308). In some embodiments, it may be efficient for the communication hub 24 to operate at a radio frequency channel having a low RSS. Furthermore, when the RSS of the scanned operating radio frequency is below a certain threshold value, the communication hub 24 may determine that a loss of data received from the sensor(s) 26 may not be caused by the interference with other sources (e.g., devices) of the interference signal (process block 310). As such, the communication hub 24 may determine that some alternative and possible causes of the sensor data loss may include sensor obstruction, a failure of the battery of the sensor, a failure in the sensing function of the sensor 26, etc. (process block 310). The communication hub 24 then sends the scanned radio frequency data 40 along with the location and time stamp corresponding to the scanned radio frequency data 40 to the radio frequency monitor 50 (process block 314).

Alternatively, when the RSS of the scanned operating radio frequency channel is above a certain threshold, the communication hub 24 may determine that it is operating at a radio frequency channel exposed to a high level of interfering signals, such that the high level of interfering signal may be coming from the other signal sources (process block 312). In some embodiments, the communication hub may determine that the high level of interfering signals (e.g., high RSS) is a result of other devices also using the operating radio frequency channel. The communication hub 24 then sends the scanned radio frequency data 40 along with the location and time stamp corresponding to the scanned radio frequency data 40 to the radio frequency monitor 50 (process block 314).

Figure 7:
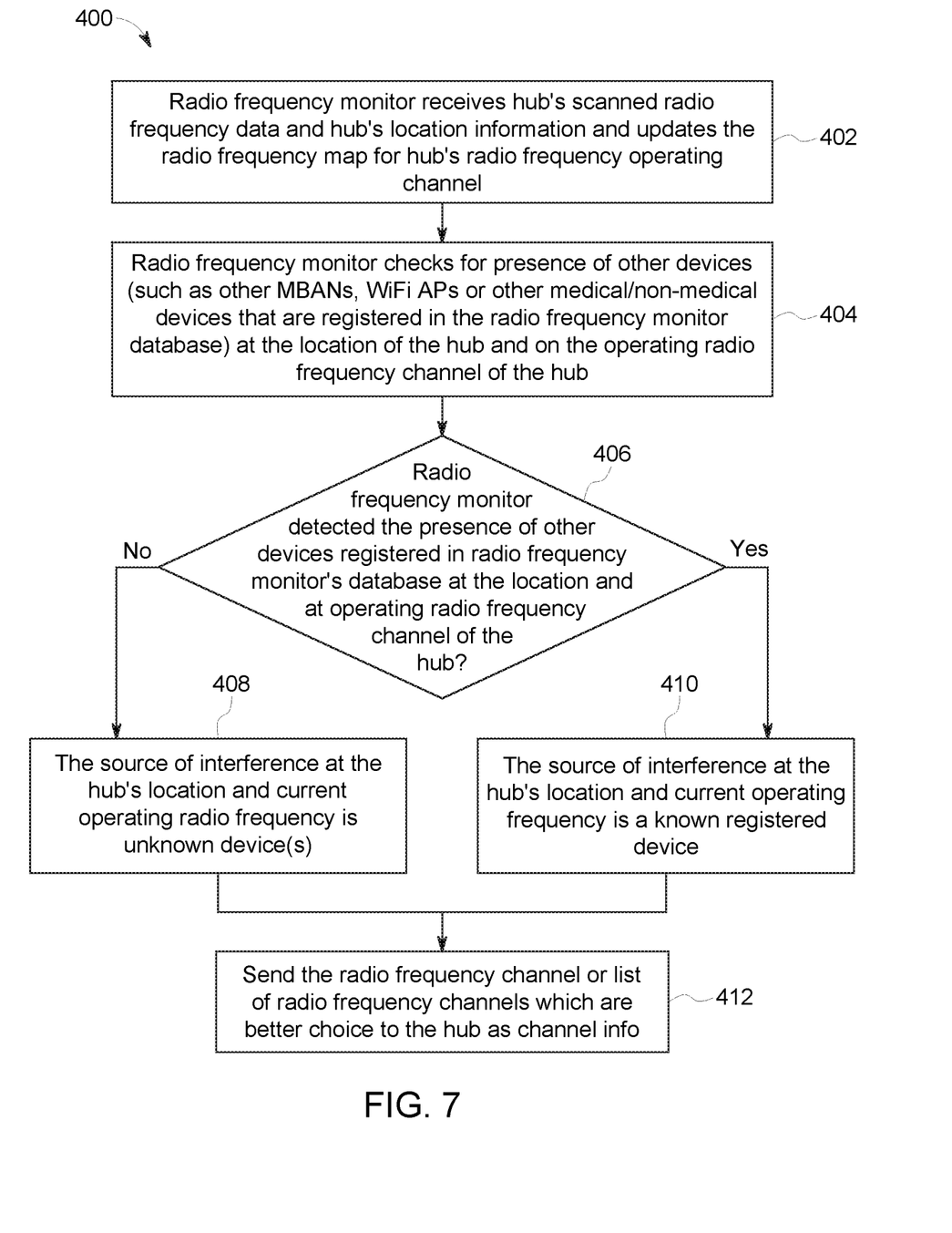
FIG. 7 is a flow diagram depicting an embodiment of a process performed by a radio frequency monitor that may be used in conjunction with the system of FIG. 1, in accordance with an aspect of the disclosure.

Turning to FIG. 7, depicted is a flow diagram 400 of an embodiment of a process performed by a radio frequency monitor 50 that may be used in the system of FIG. 1. In some embodiments, the radio frequency monitor 50 receives the scanned radio frequency data 40 from the communication hub 24 (e.g., along with the location and time information) to update the radio frequency map 70 corresponding to the operating radio frequency channel that the communication hub 24 operates in (process block 402). After receiving the radio frequency data 40, the radio frequency monitor 50 checks for the presence of other devices (e.g., MBANs 20, Wi-Fi access points, medical devices, non-medical devices registered in the radio frequency database 61) at the location of the communication hub 24 and on the operating radio frequency channel of the communication hub 24 (process block 404).

Afterwards, the radio frequency monitor 50 determines whether it detects the presence of other devices registered in the radio frequency database 61 at the location and at the operating the radio frequency channel of the communication hub 24 (decision block 406). When the radio frequency monitor 50 does not detect the presence of other devices, the radio frequency monitor 50 may determine that the source of interference at the location and current operating radio frequency corresponding to the communication hub 24 may be derived from an unknown device(s) (process block 408). Alternatively, when the radio frequency monitor 50 detects the presence of other devices, the radio frequency monitor 50 may determine that the source of interference at the location and current operating radio frequency corresponding to the communication hub 24 may be derived from a known device(s) (e.g., devices registered with the radio frequency database 61) (process block 410). The radio frequency monitor 50 may then send channel information that includes a list of radio frequency channels that may be a better choice for the communication hub 24 to use (process block 412). In some embodiments, a radio frequency channel having a low RSS (e.g., below a certain threshold value) may be a better choice of radio frequency channel for the communication hub 24 to use.

Technical effects include systems and methods for analyzing a wireless environment (e.g., of a hospital) that may allow for the transmission of data via a (e.g., hospital) communication infrastructure (e.g., Wi-Fi, cellular). More specifically, various medical sensors may transmit physiological data to a communication hub, which in turn may send the physiological data to the communication infrastructure so that it may be distributed (e.g., throughout the hospital) to various devices. A radio frequency monitor may receive radio frequency data (e.g., location of the communication hub, time stamp, and received signal strength indication) from the communication hub(s), and analyze the radio frequency data. Analyzing the radio frequency data may include measuring the received signal strength at various radio frequency channels at certain locations and instances of time and may include radio frequency maps generated by the radio frequency monitor. In some instances, when the received signal strength corresponding to a radio frequency channel is abnormally high (e.g., above a threshold strength value), the radio frequency monitor may identify the device and/or source of the anomaly. Furthermore, the radio frequency monitor may also prevent the loss of data transmission across the communication infrastructure by only allowing devices to transmit data through channels with a received signal strength below a threshold value or by communicating in a manner that may improve the transmission of data.

This written description uses examples, including the best mode, and also to enable any person skilled in the art to practice the disclosed embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
a wireless communication network, wherein the wireless communication network is configured to transmit data over a plurality of available radio frequency channels;
one or more medical sensors, wherein the medical sensors are associated with a patient and configured to detect physiological data from the patient;
one or more communication hubs associated with the patient configured to receive the detected physiological data from the one or more medical sensors and configured to scan the plurality of available radio frequency channels around the one or more communication hubs to generate radio frequency data indicative of a measured signal strength in each available radio frequency channel of the plurality of available radio frequency channels and configured to wirelessly transmit the physiological data and the radio frequency data via one or more of the available plurality of radio frequency channels;
a processor; and
a memory storing instructions, wherein the instructions are configured to cause the processor to:
receive the radio frequency data;
associate the radio frequency data from each communication hub with a respective physical location within a facility at a particular time to generate a map of the radio frequency data, wherein the map of the radio frequency data includes location data within the facility and time data and is based on the measured signal strength for each available radio frequency channel associated with a plurality of respective locations; and
provide communications instructions to the one or more communication hubs to communicate the physiological data over a different available radio frequency channel based on the map of the radio frequency data.

2. The system of claim 1, wherein the measured signal strength of each available radio frequency channel of the plurality of available radio frequency channels comprises data indicative of interfering power output of a device in the environment of the one or more communication hubs.

3. The system of claim 1, wherein the one or more medical sensors comprise a blood pressure sensor, an electrocardiogram (ECG) sensor, a pulse oximeter sensor, an electromyography (EMG) sensor, an inertial sensor, or any combination thereof.

4. The system of claim 1, wherein the physiological data comprises data indicative of blood pressure, heart rate, metabolic rate, blood oxygen concentration by volume of total blood, electrical activity, or any combination thereof.

5. The system of claim 1, wherein the wireless communication network comprise industrial, scientific, and medical (ISM) radio bands and medical body area network (MBAN) radio bands.

6. The system of claim 1, wherein the communication hub is communicatively coupled to the medical sensors via a MBAN radio frequency channel and is communicatively coupled to a hospital communication infrastructure via Wi-Fi radio frequency channels.

7. The system of claim 1, wherein the processor is configured to identify an anomaly associated with the radio frequency environment, wherein the anomaly comprises a loss in the data transmitted over a plurality of available radio frequency channels or an identification of an available radio frequency channel with a measured signal strength below a threshold value.

8. The system of claim 7, wherein the instructions that are configured to cause the processor to provide communications instructions to the one or more communication hubs is based on the anomaly.

9. A method, comprising:
receiving radio frequency data via a communication hub communicatively coupled to a medical sensor, wherein the medical sensor is associated with a patient and configured to detect physiological data from the patient, wherein the communication hub is configured to receive the detected physiological data from the one or more medical sensors and configured to scan a plurality of available radio frequency channels in a wireless communication network around the communication hub to generate radio frequency data indicative of measured signal strength of the plurality of available radio frequency channels and configured to wirelessly transmit the radio frequency data via one or more available radio frequency channels of the plurality of available radio frequency channels;
generating a radio frequency map based on the received radio frequency data, wherein the radio frequency map comprises the measured signal strength corresponding the each available radio frequency channel of the plurality of available radio frequency channels over time, the measured signal strength for each available radio frequency channel of the plurality of available radio frequency channels corresponding to a location on one or more floors of a hospital environment; and providing communications instructions to the communication hubs to communicate the physiological data over a different available radio frequency channel based on the radio frequency map.

10. The method of claim 9, wherein the different available radio frequency channel is an available radio frequency channel with a lower measured signal strength.

11. The method of claim 9, wherein generating the radio frequency map comprises updating the radio frequency map at or near real time.

12. The method of claim 11, wherein updating the radio frequency map at or near real time comprises updating at or near real time the measured signal strength corresponding the each available radio frequency channel over time and the measured signal strength corresponding to each floor of the hospital environment.

13. The method of claim 9, wherein providing communications instructions to the communication hub to communicate the physiological data over the different available radio frequency channel is based on an identification of a low measured signal strength corresponding to the one or more of the plurality of available radio frequency channels.

14. A system, comprising:
  a plurality of medical sensors and a plurality of communication hubs, wherein each medical sensor is associated with a respective patient and a respective communication hub of the plurality of communication hubs, wherein each medical sensor is configured to detect physiological data from the patient, wherein each communication hub is configured to receive the detected physiological data from the one or more medical sensors and configured to scan a plurality of available radio frequency channels around each communication hub to generate radio frequency data indicative of measured signal strength of the plurality of available radio frequency channels in a wireless communication network, and wherein each communication hub is configured to wirelessly transmit location data related to a location of the hub within a facility, the physiological data, and the radio frequency data via one or more of the plurality of available radio frequency channels;
  a radio frequency monitor, comprising:
    a processor; and
    a memory storing instructions, wherein the instructions are configured to cause the processor to:
      receive the location data and the radio frequency data from the plurality of communication hubs;
      generate a plurality of radio frequency maps based on the location data and the radio frequency data, wherein the plurality of radio frequency maps are updated based on time stamp of the location data and the radio frequency data;
      identify one or more congested radio frequency channels associated with an individual location; and
      provide communications instructions to one or more of the plurality of communication hubs associated with the individual location to communicate the physiological data to avoid the one or more congested radio frequency channel.

15. The system of claim 14, wherein the medical sensors comprise wearable sensors configured be communicatively coupled to the communication hub via a wireless connection.

16. The system of claim 14, comprising updating the instructions when the one or more of the communication hubs are no longer associated with the individual location.

* * * * *